(12) United States Patent
Kaasgaard et al.

(10) Patent No.: US 6,180,360 B1
(45) Date of Patent: *Jan. 30, 2001

(54) PROCESS OF PRODUCING β-LACTAM ANTIBIOTICS APPLYING MICRO-ORGANISMS WITH INCREASED LIGASE ACTIVITY

(75) Inventors: Svend Kaasgaard, Søborg; Klaus Kristiansen; Henrik Mølgaard, both of Lyngby, all of (DK)

(73) Assignee: Gist-Brocades, Delft (NL)

( * ) Notice: Under 35 U.S.C. 154(b), the term of this patent shall be extended for 0 days.

This patent is subject to a terminal disclaimer.

(21) Appl. No.: 09/333,645

(22) Filed: Jun. 15, 1999

Related U.S. Application Data

(63) Continuation of application No. 08/817,010, filed as application No. PCT/EP95/03857 on Sep. 27, 1995, now Pat. No. 5,942,411.

(30) Foreign Application Priority Data

Sep. 28, 1994 (DK) ..................................... 1117/94

(51) Int. Cl.⁷ ............................. C12P 35/06; C12P 37/00; C12N 9/00; C12N 1/20
(52) U.S. Cl. ................................. 435/49; 435/43; 435/44; 435/48; 435/71.1; 435/71.2; 435/71.3; 435/183; 435/252.3; 435/252.31; 435/252.33; 435/252.35; 435/254.11; 435/254.5; 435/320.1; 435/254.3; 536/23.2; 536/23.1; 536/23.7; 530/350
(58) Field of Search ................................. 435/43, 44, 48, 435/49, 71.1, 71.2, 71.3, 183, 252.3, 252.31, 252.33, 252.35, 254.11, 254.5, 254.3, 320.1; 530/350; 536/23.2, 23.1, 23.7

(56) References Cited

U.S. PATENT DOCUMENTS 5,942,411 * 8/1999 Kaasgaard et al. ..................... 435/49

FOREIGN PATENT DOCUMENTS

WO 92/07079    4/1992 (WO).
WO 97/02349    1/1997 (WO).

OTHER PUBLICATIONS

Brunner et al., *Chemical Abstracts*, 68(13), Ab. No. 56941d, 56949 (1968).
Brunner et al., *Chemical Abstracts*, 83(21), Ab. No. 174438c, 206 (1975).
Brunner et al., *Hoppe–Seyler's Z. Physiol. Chem*, 349(1), 95–103 (1968).
Brunner et al., *Methods Enzymol.*, 43, 476–481 (1975).
Kurylowicz et al., *Archivum Immunologiae et Therapiae Experimentalis*, 35(5), 699–724 (1987).
Kurylowicz et al., *Chemical Abstracts*, 111(1), Ab. No. 3885, 376 (1989).
Martinez Blanco et al., *Chemical Abstracts*, 115(17), Ab. No. 181509, 763 (1991).
Martinez Blanco et al., *Chemical Abstracts*, 117(3), Ab. No. 26135g, 26143 (1992).
Martinez Blanco et al., *Chemical Abstracts*, 119(19), Ab. No. 201862g, 754 (1993).
Martinez–Blanco et al., *Gene*, 130, 265–270 (1993).
Martinez–Blanco et al., *J. Antibiotics*, 44(11), 1252–1258 (1991).
Martinez–Blanco et al., *J. Biolog. Chem.*, 267(8), 5474–5481 (1992).

* cited by examiner

Primary Examiner—Rebecca E. Prouty
Assistant Examiner—Richard Hutson
(74) Attorney, Agent, or Firm—McDonnell Boehnen Hulbert & Berghoff

(57) ABSTRACT

The present invention relates to the biosynthesis of β-lactam antibiotics. More specifically, the invention relates to processes of producing β-lactam antibiotics in vivo and in vitro. Also contemplated is a novel enzyme capable of catalyzing certain steps involved in β-lactam biosynthesis. Further, the invention relates to a DNA construct encoding the novel enzyme, a recombinant vector or transformation vehicle comprising the DNA construct, and finally a cell comprising the DNA construct or recombinant vector.

35 Claims, 3 Drawing Sheets

PROCESS OF PRODUCING β-LACTAM ANTIBIOTICS APPLYING MICRO-ORGANISMS WITH INCREASED LIGASE ACTIVITY

CROSS REFERENCE TO RELATED APPLICATIONS

This application is a continuation of U.S. Ser. No. 08/817,010, filed Jun. 19, 1997, now allowed as U.S. Pat. No. 5,942,411, which itself is a 371 application of PCT International Application WO 96/10085 filed Sep. 27, 1995 as PCT/EP95/03857. Additionally, this application claims the priority of Denmark Application No. 1117/94 filed on Sep. 28, 1994.

FIELD OF THE INVENTION

The present invention relates to biosynthesis of β-lactam antibiotics. More specifically, the invention relates to in vivo and in vitro processes of producing β-lactam antibiotics.

Also contemplated is a novel enzyme which advantageously can be used in the β-lactam antibiotic biosynthesis. Further the invention relates to a DNA construct encoding said novel enzyme, a recombinant vector or transformation vehicle comprising said DNA construct, and finally a cell comprising said DNA construct or recombinant vector.

BACKGROUND OF THE INVENTION

Biosynthetic pathway of penicillin

The first step in the biosynthesis of penicillin involves the formation of the tripeptide δ-(L-α-aminoadipyl)-L-cysteinyl-D-valine (ACV) from L-α-aminoadipic acid, L-cysteine and L-valine (Fawcett et al., Biochem. J., 157, p. 651–660, 1976). The reaction is catalyzed by a multifunctional enzyme δ-(L-α-aminoadipyl)-L-cysteinyl-D-valine synthetase (ACV synthetase) with ATP and $Mg^{2+}$ as co-factors (Banko et al., J. Am. Chem. Soc., 109, p. 2858–2860, 1987).

ACV synthetase (ACVS) has been purified from *Aspergillus nidulans* (Van Liempt et al., J. Biol. Chem., 264, p. 3680–3684, 1989), *Cephalosporium acremonium* (Baldwin et al., J. Antibiot., 43, p. 1055–1057, 1990) and *Streptomyces clavuligerus* (Jensen et al., J. Bacteriol., 172, p. 7269–7271, 1990, and Zhang et al., Biotechnol. Lett., 12, p. 649–654, 1990). The purification of ACV synthetase from *Penicillium chrysogenum* has not been published. However, ACV synthetase from *P. chrysogenum* has been cloned by Diez et al. (J. Biol. Chem., 265, p. 16358–16365, 1990).

The linear tripeptide, ACV, is converted to isopenicillin N (IPN) in the presence of isopenicillin N synthase (also referred to as cyclase or isopenicillin N synthetase (IPNS)), ferrous ions, oxygen and an electron donor (lag ascorbate). Isopenicillin N synthase was first isolated from *P. chrysogenum* by Ramos et al. (Antimicrobial Agents and Chemotherapy, 27, p. 380–387, 1985) and the isopenicillin N synthase structural gene from *P. chrysogenum* cloned by Carr et al. (Gene, 48, p. 257–266, 1986).

These first two steps in the biosynthesis of penicillins are common in penicillin and cephalosporin producing fungi and bacteria.

In some fungi, for example in *P. chrysogenum* and in *A. nidulans*, the α-aminoadipyl side chain of isopenicillin N can be replaced by other side chains of intracellular origin or exogenously supplied. The exchange is catalyzed by an acyltransferase (referred to as acyl-coenzyme A: isopenicillin N acyltransferase or acyl-coenzyme A:6-aminopenicillanic acid acyltransferase). It is still unclear whether this conversion proceeds in vivo by a two-step reaction in which first the L-α-aminoadipyl side chain is removed to yield 6-aminopenicillanic acid (6-APA) followed by the acylation step, or the conversion is a direct exchange of the side chains. Purified acyltransferase from *P. chrysogenum* has both an isopenicillin N-amidohydrolase activity and an acyl-coenzyme A:6-aminopenicillanic acid acyltransferase activity Alvarez et al. Antimicrobial Agents and Chemotherapy, 31, p. 1675–1682, 1987).

The genes coding for ACV synthetase (pcbAB), isopenicillin N synthase (pcbC) and acyl-coenzyme A:6-aminopenicillanic acid acyltransferase (penDE) are found in the same cluster in *P. chrysogenum* and *A. nidulans* (Diez et al., J. Biol. Chem., 265, p. 16358–16365, 1990, and Smith et al., Bio/Technology, a, p. 39–41, 1990).

Amplification of the pcbC-penDE gene cluster of *P. chrysogenum* Wis 54–1255, coding for isopenicillin N synthase (IPNS) and acyltransferase (AT), respectively, led to as much as a 40% improvement in production yields (Veenstra et al., J. Biotechnol., 17, p. 81–90, 1991). Increased antibiotic yields were also reported in *A. nidulans* transformants containing multiple copies of pcbAB (coding for ACV synthetase (ACVS)) and pcbC genes (coding for isopenicillin N synthetase (INPS)) (McCabe et al., J. Biotechnol., 17, p. 91–97, 1991).

EP 200425 (Eli Lilly) discloses vectors encoding isopenicillin N synthetase (IPNS). The vectors permit high level expression of IPNS in *C. acremonium* and *E. coli*. According to the disclosure the Cephalosporium vectors are useful for strain improvement, to increase efficiency and yield in fermentations for the production of penicillin and cephalosporin antibiotics. The vectors may also be modified to give vectors for increasing the production yields and efficiency of *P. chrysogenum, Streptomyces clavuligerus* etc. in fermentations.

EP 357119 (Gist Brocades) discloses the clustered antibiotic biosynthetic genes encoding IPNS, AT and ACVS and are advantageously employed for improvement of production of the antibiotic in microorganisms and for the isolation of other genes involved in the biosynthesis of the antibiotic. The invention is exemplified with improved production of penicillin in *P. chrysogenum*, with the isolation of another clustered biosynthetic gene(s) and with the expression of clustered penicillin biosynthetic genes in *Acremonium chrysogenum*.

Activation of side chain

In order to replace the α-aminoadipic acid side chain in the acyltransferase catalyzed reaction, the carboxylic acid group of the new side chain has to be activated. This activation is one of the least well understood parts of the biosynthesis of penicillins. Two theories have been proposed.

The most widely accepted theory is that the enzyme catalyses the esterification of carboxylic acids into coenzyme A thioesters by a two-step mechanism that proceeds through the pyrophosphorolysis of ATP (adenosine triphosphate), in the presence of $Mg^{2+}$. Firstly, the carboxylic acid (the new side chain), ATP and the enzyme forms a complex, leading to an acyl-AMP-enzyme complex. Secondly, this complex reacts with coenzyme A to liberate acyl-coenzyme A and AMP (adenosine monophosphate).

The other theory is based on the formation of an acyl-S-glutathione intermediate, which may be transformed to the corresponding acyl-coenzyme A ester (Ferrero et al., J. Antibiot., 43, p. 684–91, 1990.

A phenacyl:coenzyme A ligase from *P. chrysogenum* able to catalyze the synthesis of phenoxyacetyl-coenzyme A and phenylacetyl-coenzyme A in the presence of ATP, $Mg^{2+}$, coenzyme A and phenoxy-acetic acid or phenylacetic acid has been described by Brunner, Rohr and Zinner (Hoppe-Seyler's Z. Physiol. Chem., 349, p. 95–103, 1968), Brunner and Rohr (Methods Enzymol., 43, p. 476–481, 1975; Kogekar and Deshpande, Ind. J. Biochem. Biophys., 19, p. 257–261, 1982, and by Kurzatkowski, Med. Dosw. Mikrobiol., 33, p. 15–29, 1981). According to Brunner et al., the ligase shows similar degrees of activity towards phenylacetic acid, phenoxyacetic acid and acetic acid. However, the enzyme was never purified to homogeneity.

Martinez-Blanco et al. (J. Biol. Chem., 267, p. 5474–5481, 1992) have described an acetyl-coenzyme A synthetase from *P. chrysogenum* Wis 54–1255 which not only accepts acetic acid but also phenylacetic acid as substrates in the synthesis of the corresponding acyl-coenzyme A esters just like the ligase described by Brunner et al. However, the activity towards phenoxyacetic acid is not described by Martinez-Blanco et al. According to Martinez-Blanco et al., the acetyl-coenzyme A synthetase is a homodimer ($\alpha_2$) having a molecular weight of 139,000 Dalton as determined by gel filtration and of 70,000 Dalton as determined by SDS-PAGE (sodium dodecyl sulfate polyacrylamide gel electrophoresis) and an isoelectric point: between pH 5.6 and 6.0.

The gene coding for the acetyl-coenzyme A synthetase of Martinez-Blanco et al. has been characterized by Martinez-Blanco et al. (Gene, 130, p. 265–270, 1993). The gene which was designated acuA contains five introns and codes for a polypeptide of 669 amino acids. This polypeptide has a molecular weight of 74,287.

Gouka et al. (Appl. Microbiol. Biotechnol., 38, p. 514–519, 1993) and Van Hartingsveldt et al. (WO 92/07079) have described the isolation and sequence of an acetyl-coenzyme A synthetase (facA) gene from *P. chrysogenum* coding for a protein of 669 amino acids corresponding to a molecular weight of approximately 74,000 Dalton (using an average molecular weight of 110 g/mol for each amino acid). The gene sequences of the facA gene of Gouka et al. and of acuA of Martinez-Blanco et al. showed no differences.

A detailed characterization of the phenylacyl-coenzyme A ligases described by Brunner et al. and by Kogekar and Deshpande has not been published.

In its activated form, the new side chain which is to replace the $\alpha$-aminoadipic acid side chain in the acyl transferase catalyzed reaction may be in the form of a coenzyme A thioester or another thioester, since other thioesters (e.g. acyl-S-cysteinyl-glycine and acyl-S-glutathione) have been reported to be substrates for the acyltransferase. As a further possibility, the dipeptide (cysteinyl-glycine) may be substituted by CoASH in a non-enzymatic reaction before it enters into the acyltransferase reaction (Ferrero et al., J. Biol. Chem., 265, p. 7084–7090, 1990).

Once it is formed, the thionylgroup of the thioesters may exchange rapidly with other thiols (e.g. mercaptoethanol, 1,4-dithithreitol, ACV and coenzyme A) in a non-enzymatic reaction.

Ligases in general

Ligases, belonging to the enzyme subclass 6.2.1., Acid-Thiol ligases (enzyme Nomenclature, Academic Press, inc., 1992) also referred to as acyl-coenzyme A synthetases or acyl-coenzyme A thiokinases, catalyze the formation of acyl-coenzyme A thioesters from a carboxylic acid and coenzyme A in the presence of ATP and $Mg^{2+}$.

Several ligases or acyl-coenzyme A synthetases from various sources have been identified e.g. acetyl-coenzyme A synthetase, propionyl-coenzyme A synthetase (Groot, Biochim. Biophys. Acta, 441, p. 260–267, 1976); butyryl-coenzyme A synthetase (Wanders et al., J. Biol. Chem., 240, p. 29–33, 1965); medium-chain, long-chain and very long-chain fatty acyl-coenzyme A synthetases (Waku, Biochim. Biophys. Acta, 1124, p. 101–111, 1992, review); benzoyl-coenzyme A ligase from Pseudomonas sp (Auburger, Appl. Microbiol. Biotechnol., 37, p. 789–795, 1992) and phenylacetyl-coenzyme A ligases (Martinez-Blanco et al., J. Biol. Chem., 265, p. 7084–7090, 1990; and Vitovski (FEMS Microbiol. Letters, 108, p. 1–6, 1993). Most of them have broad substrate specificities.

The acyl-coenzyme A synthetases (ligases) are generally key enzymes in the primary metabolism of fatty acids and acetic acid and in the initial steps in the degradation of aromatic acids where they through the formation of the energy-rich thioester bond activate the acyl group of the carboxylic acid.

In vivo production of $\beta$-lactams

Many of the so called natural $\beta$-lactams (e.g. penicillin DF, isopenicillin N, 6-APA, cephalosporin C etc.) are unstable, difficult to purify from the fermentation broth, have only limited antibiotic effect, and/or are produced in low yield.

Replacing the side chains of the natural $\beta$-lactams with e.g. phenoxyacetic acid or phenylacetic acid leads to the formation of penicillins (penicillin V and penicillin G, respectively), which are more stable, easier to isolate and having a higher antibiotic activity.

The only directly fermented penicillins of industrial interest are penicillin V and penicillin G, produced by adding phenoxyacetic acid or phenyllactic acid, respectively to the fermentation tank. Addition of alternative precursors, for example 2-thiopheneacetic acid or 3-thiopheneacetic acid, during the fermentation of *P. chrysogenum* leads to other penicillins. Some added precursors e.g. 1-phenyl-n-alkanes or 1-phenoxy-n-alkanes may be partly metabolized within the *P. chrysogenum* cells before being used a substrate for the acyltransferase in the production of penicillins (Szarka, Advances in Biotechnology, 3, p. 167–173, 1980; Szarka et al., U.S. Pat. No. 4,250,258; and Szarka et al., U.S. Pat. No. 4,208,481). In the biosynthesis of the so-called natural penicillins: e.g. penicillin DF, penicillin K, penicillin F and penicillin H; the side chains: hexanoic acid, octanoic acid, 3-hexenoic acid, and heptanoic acid, respectively, are presumably derived from the primary metabolism.

In some cases the phenoxyacetyl or the phenylacetyl side chain also acts as a protection group during the fermentation and recovery of the $\beta$-lactam, as the isolated penicillin V or G are hydrolysed by an organic chemical or enzymatic process to form 6-APA, which, in turn is the basic building block for new semi-synthetic penicillins having improved pharmacological properties compared to the natural penicillins as-well as the penicillin V or G.

Likewise in the production of cephalosporins, the natural cephalosporins are of limited pharmaceutical value, as they too are difficult to isolate and have only a low antibiotic effect. Furthermore, they are difficult to transform into new cephalosporins of higher pharmaceutical value.

A number of steps have to be carried out, in order to transform the fermented cephalosporin into the desired antibiotic. e.g. in the production of the oral cephalosporins cephalexin and cefadroxil, the starting point is penicillin V or G, which is then transformed into a cephalosporin by a series of chemical reactions, keeping the phenoxyacetyl or phenylacetyl side chain as a protection group. After the ring expansion V-DCA or G-DCA (V/G-deacetoxycephalosporanic acid), respectively, is formed, the side-chain is removed by hydrolysis in a process similar to the hydrolysis of penicillin V or G. Finally, a new sidechain (e.g. D-phenylglycine or D-p-hydroxy-phenylglycine) is added by an organic chemical process.

In the production of cephalosporins from cephalosporin C, the D-α-aminoadipic acid may be removed either by chemical hydrolysis or by a two step organic chemical enzymatic process. The resulting 7-ACA (7-amino cephalosporanic acid) is then acylated to form the desired product.

Both the reactions leading to the formation of V-DCA, G-DCA and the hydrolysis of cephalosporin C to 7-ACA are carried out in industrial scale but they are difficult to control, expensive and yields generally are low.

In order to circumvent this problem, several alternatives have been suggested some of which involves the transformation of P. chrysogenum with the epimerase and expandase from e.g. Streptomyces, as described by C. Cantwell et al., 248, p. 283–289, 1992. They demonstrated the transformed P. chrysogenum was able to produce deacetoxycephalosporanic acid. However, no V-DCA was found. Cantwell suggested the expandase may be modified by genetic engineering in order to change its substrate specificity to accept penicillin V or G as substrate. Then the V/G-DCA may be produced directly by fermentation.

S. Gutiérrez et al., Mol. Gen. Genet., 225, p. 56–64, 1991, transformed C. acremonium with the acyltransferase from P. chrysogenum, and were able to detect penicillin G formation by the transformed C. acremonium, but the presence of G-DCA was not proved.

EP 532341 (Merck & Co, Inc.) describes the fermentation of adipoyl-7-ADCA (adipoyl-7-aminodesacetoxycephalosporanic acid) in P. chrysogenum transformed with the expandase from Streptomyces clavuligerus. The adipoyl-7-ADCA can then be extracted from the fermentation broth and hydrolysed by an adipoyl acylase from e.g. Pseudomonas.

ES 2,016,476 discloses in vitro bio-chemical preparation of phenylacetyl-coenzyme A and benzyl penicillin (penicillin G). Phenylacetyl-coenzyme A is made by incubating phenyl-acetyl-coenzyme A ligase from Pseudomonas putida with ATP, phenylacetic acid and $MgCl_2$ at 10–45° C. and pH 5–10 for 10–180 minutes. Benzyl penicillin is made by incubating the phenylacetyl-coenzyme A ligase and acyl-coenzyme A:6-aminopenicillanic acid acyl transferase from Penicillium chrysogenum with 6-aminopenicillanic acid and phenylacetic acid, ATP, coenzyme A and $MgCl_2$ at 10–40° C. and pH 5.5–9 for 30–180 minutes.

ES 2,033,590 discloses ji vitro production of different penicillins derived from benzyl penicillin (penicillin G). The production comprises incubating an enzyme system containing phenylacetyl-coenzyme A ligase from Pseudomonas putida and acyl-coenzyme A-aminopenicillanic acid acyl-transferase of Penicillium chrysogenum, and substrates, such as 6-amino penicillanic acid, ATP, coenzyme A, $MgCl_2$, dithiotreitol (DTT) and precursors of the penicillins.

In the Prior art processes have been disclosed for the production of certain penicillins and cephalosporins that include in vitro steps. Mostly these processes are difficult to control, cumbersome and/or expensive.

SUMMARY OF THE INVENTION

It is the object of the invention to overcome some of the problems described above. This is done by providing improved processes of producing β-lactam antibiotics, which processes take place in the presence of increased ligase activity in comparison to the ligase activity present when fermenting with said original microorganism alone, under the original fermentation conditions.

The invention also relates to a novel enzyme exhibiting ligase activity which has a high substrate specificity towards important β-lactam precursors, such as phenoxyacetic acid, phenylacetic acid and adipic acid and a low specificity towards acetic acid.

According to the invention the enzyme may be derived from the filamentous fungi Penicillium chrysogenum, Aspergillus nidulans or Cephalosporium acremonium.

The novel enzyme can be used in connection with biosynthesis of various β-lactam antibiotics.

It is also an object of the invention to provide a method for producing β-lactam antibiotics in vitro.

Also contemplated is a DNA construct encoding said novel enzyme exhibiting ligase activity.

Further, it is the object of the invention to provide a recombinant vector or transformation vehicle comprising said DNA construct.

Also contemplated according to the invention is a cell comprising said DNA construct or said recombinant vector.

BRIEF DESCRIPTION OF TEE DRAWINGS

DETAILED DESCRIPTION OF THE INVENTION

Figure 1:
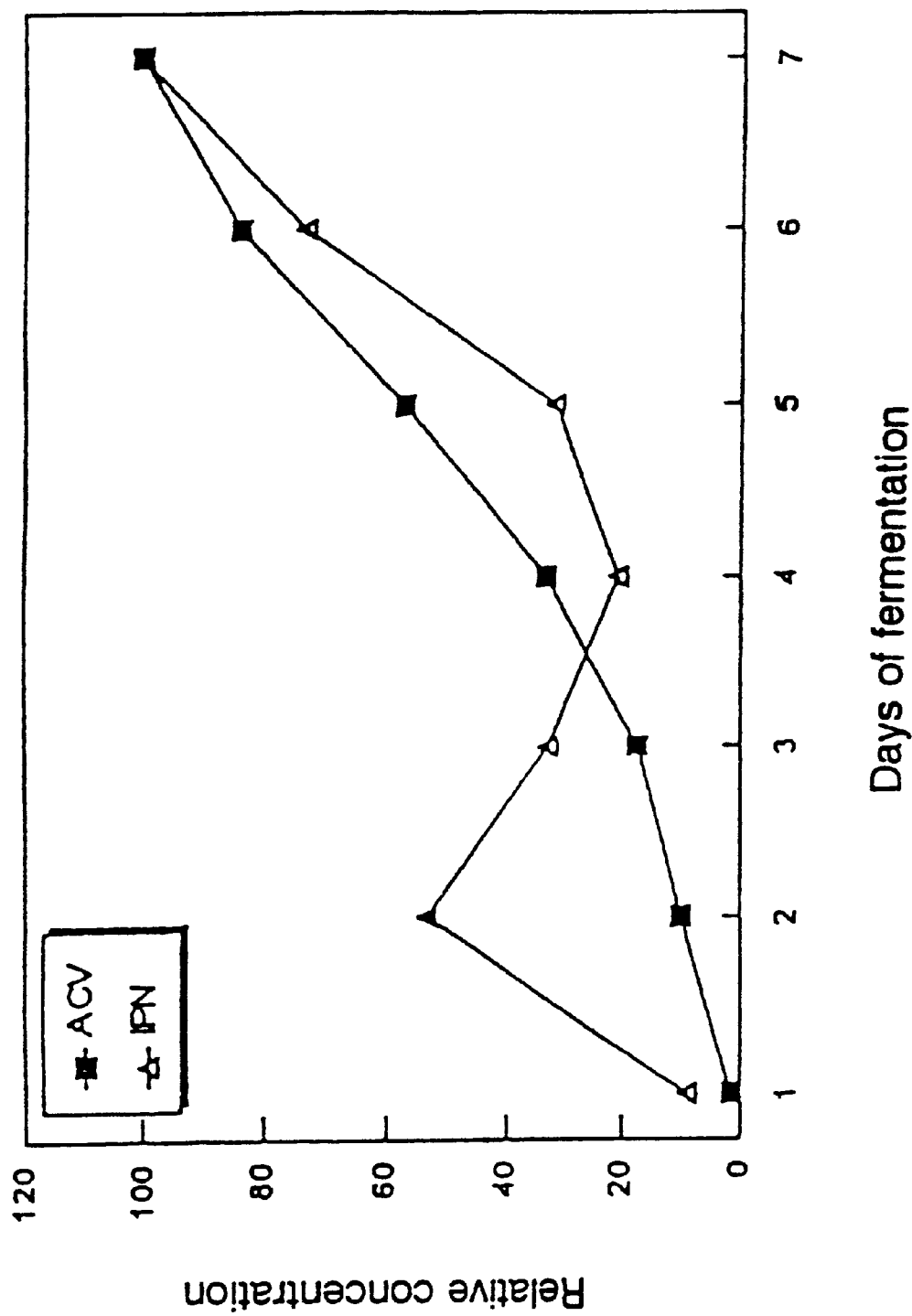
FIG. 1 shows the concentrations of ACV and isopenicillin N as a function of the fermentation period.

As the production economy is an important factor in the production of β-lactams, improved processes leading to an increased fermentation yield, processes which are easier to control and being less cumbersome, and consequently less expensive, are needed.

It is the object of the invention to provide such improved processes for producing β-lactam antibiotics.

It has now surprisingly been found that such improved processes can be provided if the production of β-lactam antibiotics of interest takes place in the presence of increased ligase activity.

According to the invention, such improved process of producing a β-lactam antibiotic, comprises i) fermentation of a microorganism capable of producing said β-lactam antibiotic, and ii) recovering said β-lactam antibiotic in substantially pure form, wherein said fermentation takes place in the presence of increased ligase activity, in comparison to the ligase activity present when fermenting with the original microorganism alone under the original fermenting conditions.

An increased ligase activity is defined as an enhanced conversion of the carboxylic acid in question towards the corresponding acyl-coenzyme A ester, in comparison to the unmodified original microorganism and/or the original fermentation conditions.

In an embodiment of the invention said original microorganism, capable of producing β-lactams, lacks or has only low ligase activity.

The increased expression of ligase activity may be accomplished by any suitable way.

As an example, according to an embodiment of the invention, the ligase activity may be increased by modulation of the physical conditions of the fermentation process, such as temperature and pH. Another possibility is subjecting the microorganism to compounds or agents, leading to an increased expression of ligase. The nature of said compound or agent depends on e.g. the promoter used for initiating the expression of the ligase. Further, by interfering with the cellular control mechanisms controlling the ligase expression increased expression of ligase activity can be achieved.

In an embodiment of the invention said ligase activity or increased ligase activity is obtained by modifying said microorganism.

This can be done by well known procedures, such as introducing at least one copy of a DNA construct or a recombinant vector, comprising a gene encoding an enzyme exhibiting ligase activity, into said original microorganism to be fermented.

In an embodiment the ligase activity or increased ligase activity is obtained by random or site specific mutagenesis of said microorganism.

Furthermore, said modification, leading to increased ligase activity, may be obtained by amino acid substitutions, deletions or additions of the ligase enzyme, as described below.

Alternatively said ligase activity or increased ligase activity is obtained by adding enzyme exhibiting ligase activity during the production of the β-lactam antibiotic.

In an alternative embodiment said DNA construct is derived from a species different from the microorganism in which it is to be introduced.

The introduction of the DNA construct or transformation vehicle may the performed by well known methods as described below.

In certain cases it is desirable to move the entire biosynthesis of a β-lactam, including the expression of the enzyme exhibiting the ligase activity to another microorganism, which is not itself capable of producing said β-lactam. This may be the case if the recipient (host) microorganism e.g. 1) is easier transformed, 2) is able to express the biosynthetic enzymes at high levels 3) has better growth characteristics or 4) produce less impurities, which may interfere with the recovery. Thus, a higher overall yield of the β-lactam may be obtained.

Alternatively new biosynthetic routes may be desirable in an organism.

According to the invention the above mentioned recipient or host microorganism is from the group comprising Penicillium, Cephalosporium, Aspergillus, Nocardia, Streptomyces, Bacillus, Cerospora, Microspora, other Eubacteria, other Actinomycetes or filamentous fungi.

In a preferred embodiment said microorganism belongs to the species from the group comprising *Penicillium chrysogenum, Penicillium notatum, Cephalosporium acremonium, Aspergillus nidulans, Nocardia lactamdurans* and *Streptomyces clavuligerus.*

In an embodiment of the invention the expression of said ligase activity is synchronized to the expression of other genes belonging to the β-lactam biosynthetic pathway. Said genes may e.g. be the pcbAB, pcbC and/or penDE genes.

The above mentioned β-lactam antibiotic is from the group comprising penicillins, cephalosporins, cephamycins, mono-bactams, and nocardicins.

Preferably said antibiotic is a cephalosporin or a penicillin, such as penicillin V, penicillin G, V-DCA, G-DCA, δ-(L-α-5-amino-5-carboxyvaleramido)-cephalosporanic acid (isocephalosporin C), adipoyl-7-ADCA, or adipoyl-7-ACA.

In an embodiment of the invention the culturing of said microorganism takes place under conditions inducing expression of said DNA sequence resulting in the production of the activated side chain coenzyme A thioester, which, in turn in the presence of an acyltransferase (AT) leads to the formation of a β-lactam containing the said side chain.

The culturing of said modified microorganism preferably takes place under conditions inducing the expression of said DNA construct or recombinant vector, thus resulting in an increased production of the coenzyme A thioester of the acid corresponding to the side chain in the desired β-lactam antibiotic, which, in turn, enables an increased flux through the step of the biosynthesis of the β-lactam in which the β-lactam side chain is introduced in the β-lactam nucleus.

Further the culturing of the microorganism may also take place under conditions, dependent on the promoter, inducing expression of said ligase.

In the specific case of producing penicillin V or penicillin G, increasing the activity of ligase by e.g. genetic engineering will lead to an increased metabolic flow through the last step in the biosynthesis.

The advantages of the improved processes, according to the invention, is firstly, a process, according to the invention, which may result in a significantly elevated accumulated yield of the β-lactam antibiotic of interest.

Secondly, due to formation of less waste product(s), the recovery and purification of β-lactam antibiotics, in substantially pure form, is facilitated.

Thirdly, the invention permits the production of the β-lactam antibiotics of interest, without the production of a significant amount of waste products. Consequently this makes the processes more efficient, due to more energy available to synthesize the products of interest. Further the waste-products may interfere adversely with the biosynthetic pathway.

Fourthly, the yield of the β-lactam antibiotic of interest is, at any time in the fermentation process, significantly elevated in comparison to fermentation processes with microorganisms lacking or having low activity of said ligase. In this context the yield may be an overall yield or the yield over a certain period of time.

All the above mentioned advantages make the processes of producing industrial important β-lactam antibiotics less expensive.

In the cases of producing penicillin V and penicillin G, where an accumulation of ACV and isopenicillin N is observed during the fermentation, an increase of the ligase activity, according to the invention, will lead to a decrease of the accumulation of said intermediate metabolites, when the conversion of isopenicillin N to penicillin V is a "bottle neck".

The expression of ligase activity or just an increase of said ligase activity, in microorganisms lacking or having low ligase activity, according to the invention, can make non-enzymatic removal of side-chains of β-lactam antibiotic intermediates superfluous in the production of e.g. penicillins and cephalosporins.

Further, the recovery and subsequent enzymatic hydrolysis of the fermented β-lactams can be facilitated if the side chains of the so called natural β-lactams are replaced by hydrophobic side chains, such as phenoxyacetic acid or phenylacetic acid, which are easily removable by enzymatic hydrolysis using penicillin V acylases or penicillin G acylases, which are well known in the β-lactam industry in the production of 6-APA.

Consequently this opens the possibility of producing certain industrial important β-lactam antibiotic intermediates in vivo, such as V-DCA and G-DCA.

According to the invention it has been found that it is possible to produce certain β-lactam antibiotics using entirely enzymatically catalyzed processes, consequently without any use of chemical processes.

In an embodiment of the invention V-DCA or G-DCA is produced entirely, by enzymatic means in vivo, by inducing the host microorganism to express an increased ligase activity, according to the invention. Further present is an acyltransferase (AT) (e.g. the acyl-coenzyme A:isopenicillin N acyltransferase from *P. chrysogenum*) and enzymes able to transform penicillins into cephalosporins (e.g. expandase from *S. clavuligerus*).

The invention also relates to a novel enzyme which may be used according to the invention.

Recently a suitable novel enzyme, exhibiting ligase activity, has been obtained and characterized.

This novel enzyme, according to the invention is an acyl-coenzyme A synthetase (ligase) and lead to an increased flow towards the product of interest, when producing β-lactam antibiotics.

A characteristic of the enzyme, according to the invention, is that it has a high specificity towards certain important industrial β-lactam antibiotic precursors.

As the ligase of this invention has no apparent activity towards acetic acid, an increased expression of the ligase activity is not likely to interfere with the intracellular availability of the acetyl-coenzyme A, one of the key metabolites in the primary metabolism. Thus, the risk of interfering adversely with the primary metabolism is reduced compared to manipulations (e.g. genetically or chemically), leading to increased expression of ligase having both activity towards acetic acid and phenylacetic acid and/or phenoxyacetic acid and/or adipic acid.

More specifically the novel enzyme, according to the invention, is at least between 10 and 100 times, preferably $10^3$ times and more preferred up to between $10^4$ and $10^5$ times more active towards phenoxyacetic acid than towards acetic acid.

Further, the enzyme, according to the invention, has a substrate specificity of at least between 10 and 100 times, preferably 103 times and more preferred up to between $10^4$ and $10^5$ times more active towards phenylacetic acid than towards acetic acid.

The enzyme of the invention is as mentioned above an acyl-coenzyme A synthetase, more specifically a phenoxyacetyl-coenzyme A synthetase and will in the following be referred to as "ligase".

The apparent molecular weight of a catalytic active form of the ligase is in the range of between 40,000 and 60,000 Dalton, specifically about 50,000 Dalton, as determined by gel filtration.

The ligase has an apparent activity optimum in the range of pH 7.0 to 9.0, in particular in the range of pH 8.0 to 8.5. In vitro the enzyme exhibits only low activity at pH 7 or below, probably due to the low stability of the ligase when kept at pH below 7.5.

The optimum temperature for ligase activity is between 35° C. and 45° C. with the highest activity at about 40° C.

The isoelectric point (pI) of the ligase appears to be higher than pH 7.25, more likely above pH 9, and below up to about pH 12.

The enzyme can be purified from cell extracts of *P. chrysogenum* by precipitation by ammonium sulphate and by elution from columns packed with various gels (e.g. Phenylsepharose, Cibacron blue and Sephacryl® S-200). An example of purification of the ligase is given below. However, other well known procedures used in the purification of proteins can be employed, e.g. other column materials may be used such as Reactive Red, Sepharose® Q FF and Sepharose S FF.

According to the present invention it has been shown that said ligase is able to catalyze the formation of phenoxyacetyl-coenzyme A, phenylacetyl-coenzyme A, adipoyl-coenzyme A and hexanoyl-coenzyme A from $Mg^{2+}$, ATP, CoASH and phenoxyacetic acid, phenylacetic acid, adipic acid or hexanoic acid, respectively. When assayed in the same systems (e.g. as described in the examples below) the ligase does not show any significant activity towards acetic acid.

The enzyme is unstable in vitro, but addition of ATP, $Mg^{2+}$ and mercaptoethanol, dithiothreitol (DTT), ascorbic acid or other reducing agents stabilizes the activity during purification and storage significantly. The presence of a high concentration of ammonium sulphate or glycerol also stabilizes the enzyme.

Based on the consumption of CoASH in the assay the activity towards phenylacetic acid is approximately 80% of the activity towards phenoxyacetic acid, under the test conditions described below in example 6.

Only when assayed in the absence of other thiols (e.g. mercaptoethanol, dithiotreitol (DTT)), a direct phenoxyacetyl-coenzyme A synthetic activity was observed. However, incubation of ligase with ATP, $Mg^{2+}$, CoASH, phenoxyacetic acid and e.g. mercaptoethanol leads to the formation of a compound which has the same UV-spectrum as the thioester of phenoxyacetic acid and mercaptoethanol, phenoxyacetyl-S—$CH_2$—$CH_3$, which also can act as a substrate for the acyltransferase (AT).

In an embodiment of the invention, said enzyme is immunoreactive with an antibody raised against a purified ligase, of the invention, derived from *Penicillium chrysogenum* strain B10.

The immunochemical properties of the enzyme can be determined immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publications, chapters 5 and 14, 1983. The terms "antigenic identity" and "partial antigenic: identity" are described in the same book, chapters 5, 19 and 20.

The enzyme according to the invention is a polypeptide.

In the present context enzymes according to the invention include mature proteins or precursor forms thereof and functional fragments thereof which essentially have the activity of the full-length polypeptides.

Further contemplated according to the invention are homologues of said enzymes. Such homologues comprise an amino acid sequence exhibiting a degree of identity of at least between 50% and 70%, better between 70% and 80%, even better up to 100%, with the amino acid sequence of the enzyme according to the present invention.

The degree of identity may be determined by conventional methods, see for instance: Altshul et al., Bull. Math. Bio., 48, p. 603–616, 1986, and Henikoff and Henikoff, Proc. Natl. Acad. Sci. USA, 89, p. 100915–10919, 1992. Briefly, two amino acid sequences are aligned to optimize the alignment scores using a gab opening penalty of 10, a gap extension penalty of 1, and "blosum 62" scoring matrix of Henikoff and Henikoff, supra.

Alternatively, the homologue of the enzyme according to the invention may be one encoded by a nucleotide sequence hybridizing with an oligonucleotide probe prepared on the basis of the nucleotide sequence of said enzyme exhibiting ligase activity.

Molecules to which the oligonucleotide probe hybridizes under these conditions are detected using standard detection procedures (e.g. Southern blotting).

Homologues of the present polypeptide may have one or more amino acid substitutions, deletions or additions. These changes are preferably of a minor nature, that is conservative amino acid substitutions that do not adversely affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., Protein Expression and Purification, 2, p. 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active enzyme. Amino acids essential to the activity of the enzyme of the invention, and therefore preferably not subject to substitution, may be identified according to procedures known in the art, such as site-directed mutagenesis or alanine-scanning mutagenesis (Cunningham and Wells, Science, 244, p. 1081–1085, 1989). In the latter technique mutations are introduced at every residue in the molecule, and the resultant mutant molecules are tested for biological activity (e.g. ligase activity to identify amino acid residues that are critical to the activity of the molecule. Sites of ligand-receptor interaction can also be determined by analysis of crystal structure as determined by such techniques as nuclear magnetic resonance, crystallography or photoaffinity labelling. See, for example, de Vos et al., Science, 255, p. 306–312, 1992; Smith et al., J. Mol. Biol., 224, p. 899–904, 1992; Wlodaver et al., FEBS Lett., 309, p. 59–64, 1992.

The homologue may be an allelic variant, i.e. an alternative form of a gene that arises through mutation, or an altered enzyme encoded by the mutated gene, but having substantially the same activity as the enzyme of the invention. Hence mutations can be silent (no change in the encoded enzyme) or may encode enzymes having altered amino acid sequence.

The homologue of the present enzyme may also be a species homologue, i.e. an enzyme with a similar activity derived from another species.

A homologue of the enzyme may be isolated by preparing a genomic or cDNA library of a cell of the species in question, and screening for DNA sequences coding for all or part of the homologue by using synthetic oligonucleotide probes in accordance with standard techniques, e.g. as described by Sambrook et al., Molecular Cloning: A Laboratory Manual, 2nd. Ed., Cold Spring Harbor Laboratory, Cold Spring Harbor, New York, 1989, or by means of polymerase chain reaction (PCR) using specific primers as described by Sambrook et al., supra.

Further homologues of the present enzyme are those which are immunologically cross-reactive with antibodies raised against the enzyme of the invention.

Another object of the invention is to provide a DNA construct encoding said enzyme exhibiting ligase activity.

As used herein the term "DNA construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a polypeptide of interest. The construct may optionally contain other nucleic acid segments.

The DNA construct of the invention, encoding the polypeptide of the invention, may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed., Cold Spring Harbor Laboratory, Cold Spring Harbor, New York, 1989). For the present purpose, the DNA sequence encoding the polypeptide is preferably of filamentous fungi- or bacterial origin.

The DNA construct of the invention encoding the polypeptide may also be prepared synthetically by established standard methods, e.g. the phosphoamidite method described by Beaucage and Caruthers, Tetrahedron Letters, 22, p. 1859–1869, 1981, or the method described by Matthes et al., EMBO Journal, 3, p. 801–805, 1984. According to the phosphoamidite method, oligonucleotides are synthesized, e.g. in an automatic DNA synthesizer, purified, annealed, ligated and cloned in suitable vectors.

Furthermore, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The DNA acid construct may also be prepared by polymerase chain reaction using specific primers, for instance as described in U.S. Pat. No. 4,683,202 or Saiki et al., Science, 239, p. 487–491, 1988. In a preferred embodiment of the invention the DNA sequence is derivable from a filamentous fungus belonging to genus of Aspergillus, Penicillium or Cephalosporium, preferably from a strain of *P. chrysogenum*, *C. acremonium*, or *A. nidulans*, especially *P. chrysogenum* strain B10.

In a further aspect, the present invention relates to a recombinant vector or transformation vehicle comprising said DNA construct of the invention encoding said enzyme exhibiting ligase activity. The recombinant vector into which the DNA construct of the invention is inserted may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the polypeptide of the invention is operably linked to additional segments required for transcription of the DNA. In general, the expression vector is derived from plasmid or viral DNA, or may contain elements of both. The term, "operably linked" indicates that the segments are arranged so that they function in concert. for their intended purposes, e.g. transcription initiates in a promoter and proceeds through the DNA sequence coding for the polypeptide.

The promoter may be any DNA sequence which shows transcriptional activity in the host cell of choice and may be derived from genes encoding proteins either homologous or heterologous to the host cell.

Examples of suitable promoters for use in filamentous fungus host cells are, for instance, the ADH3 promoter (McKnight et al., The EMBO J., 4, p. 2093–2099, 1985) or the tpiA promoter. Examples of other useful promoters are those derived from the gene encoding A. oryzae TAKA amylase, Rhizomucor miehei aspartic proteinase, A. niger neutral α-amylase, A. niger acid stable α-amylase, A. niger or A. awamori glucoamylase (gluA), Rhizomucor miehei lipase, A. oryzae alkaline protease, A. oryzae triose phosphate isomerase or A. nidulans acetamidase. Preferred are the TAKA-amylase and gluA promoters.

It is often advantageous to use identical or similar promoters to regulate two or more of the biosynthetic genes in order to obtain a synchronized production of the intermediates involved in the β-lactam antibiotic synthesis. If the production of intermediates is not synchronized an accumulation of intermediates (bottle neck) might arise. Consequently the production of β-lactam antibiotic may be retained.

In an embodiment of the invention the promoter of said ligase gene is replaced by the promoter from another gene involved in the biosynthesis of β-lactams.

A specific example of a suitable promoter is the AT promoter described in the not published Danish patent application No. 1118/94.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis*alkaline protease gen, or the *Bacillus pumilus* xylosidase gene, or by the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may advantageously comprise a DNA sequence enabling the vector to replicate in the host cell in question.

The recombinant vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene, 40, p. 125–130, 1985), or one which confers resistance to a drug, e.g. ampicillin, kanamycin, tetracyclin, phleomycin, chloramphenicol, neomycin, hygromycin or methotrexate.

For filamentous fungi, selectable markers include amdS, pyrG, argB, niaD, and sC.

To direct a ligase enzyme of the present invention to the desired location within the host cell or into the fermentation media, a targeting signal or a secretory signal sequence (also known as a leader sequence, prepro sequence or pre sequence), respectively, may be provided in the recombinant vector. The targeting signals or secretory signal sequence are joined to the DNA sequence encoding the enzyme in the correct reading frame. Secretory sequences are commonly positioned 5' to the DNA sequence encoding the enzyme, whereas the targeting signal sequences are commonly positioned 3' to the DNA sequence. The targeting signal or secretory signal sequences may be that normally associated with the enzyme or may be from a gene encoding another protein having the desired signal sequence.

For use in filamentous fungi, the signal peptide may conveniently be derived from a gene encoding an Aspergillus sp. amylase or glucoamylase, a gene encoding a *Rhizomucor miehei* lipase or protease, a *Humicola lanuginosa* lipase etc. The signal peptide is preferably derived from a gene encoding A. oryzae TAKA amylase, A. niger neutral α-amylase, A. niger acid-stable amylase, or A. nicer glucoamylase.

According to the present invention the targeting sequence is preferably a targeting signal capable of directing the ligase activity to the desired location within the cell (e.g. to the microbodies). It is often desirable that potential targeting signals are maintained. However, the targeting signal may be replaced with other signals having the same function. Furthermore, if inserting the ligase coding sequence, lacking a suitable ligase targeting signal, into an organism, it may be added in order to have the ligase expression at the desired localization within the host cell.

For the use in filamentous fungi, an example of a peroxisomal targeting signal (PTS), with the ability to translocate cytosolic passenger proteins to the peroxisomes (classified as microbodies), in e.g. *Neurospora crassa* is described by Keller et al., J. Cell Biol., 114, p. 893.–904, 1991).

The procedures used to ligate the DNA sequences coding for the present enzyme, the promoter and optionally the terminator and/or secretary signal sequence or targeting signal sequence respectively, and to insert them into suitable vectors containing the information necessary for replication, are well known to persons skilled in the art (cf. Sambrook et al., Molecular Cloning: A Laboratory Manual, 2nd. Ed. Cold Spring Harbor Laboratory, Cold Spring Harbor, New York, 1989).

It is further the object of the invention to provide a cell comprising a DNA construct or a recombinant vector according to the invention.

The DNA sequence encoding the present polypeptide introduced into the host cell may be either homologous or heterologous to the host in question. If homologous to the host cell, i.e. produced by the host cell in nature, it may be operably connected to an other promoter sequence or, if applicable, another secretory signal sequence and,/or terminator sequence than in its natural environment. The term "homologous" is intended to include a cDNA, semi-synthetically or synthetically produced DNA, sequence encoding a polypeptide native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which can be made capable of producing the present polypeptide (enzyme) and includes preferably filamentous fungi and bacteria cells.

Examples of bacterial host cells which, on cultivation, will be capable of producing the enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, or strains of Streptomyces, such as *S. lividans, S. murinus* or *S. clavuligarus*, or gram-negative bacteria such as *Escherichia coli*. The transformation of the bacteria may be effected by protoplast transformation or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the polypeptide is refolded by diluting the denaturing agent. In the latter case, the enzyme may be recovered from the periplasmic space by disrupting the cells, e.g. by sonication or osmotic shock, to release the contents of the periplasmic space and recovering the enzyme.

Examples of cells of filamentous fungi are, e.g. Penicillium spp., Aspergillus spp., Neurospora spp., Fusarium spp., Trichoderma spp. or Cephalosporins spp., in particular strains of *P. chrysogenum, P. notatum, A. oryzae, A. nidulans, A. niger*, or *C. acremonium*. Fungal cells may be transformed by a process involving protoplast formation and transformation of the protoplasts followed by regeneration of the cell wall in a manner known per se. The use of Aspergillus spp. for the expression of proteins is described in, e.g., EP 272 277, EP 238 023 and EP 184 438. The transformation of *F. oxysporum* may, for instance, be carried out as described by Malardier et al., 1989, Gene 78, p. 147–156.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

The transformed or transfected host cell described above is then cultured in a suitable nutrient medium under conditions permitting the expression of the present enzyme, after which the resulting enzyme may be recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

The enzyme produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic and/or electrophoretic procedures, e.g. ion exchange chromatography, gelfiltration chromatography, isoelectric focusing, affinity chromatography, or the like, dependent on the type of polypeptide in question.

In the case of the enzyme being present intracellularly in the host cell, the cells are initially recovered from the fermentation media by centrifugation or filtration. Then the cells are subjected to a homogenization to open the cells, then the proteinaceous components of the supernatant or filtrate are precipitated by means of a salt as mentioned above. Finally the enzyme is purified as described above. In an embodiment of the invention the host cell, in which the bacterial cell is a cell of a gram-positive bacterium, e.g. of the genus Bacillus or Streptomyces or a cell of a gram-negative bacterium, e.g. of the genus Escherichia, and the filamentous fungus is e g. of the genus Aspergillus, Cephalosporium, or Penicillium.

In a preferred embodiment the host cell is *P. chrysogenum* and *C. acremonium*.

Methods and Materials
Strains:
B10: *P. chrysogenum* strain (available from Panlabs, 11804 North Creek Parkway South, Bothell Wash. 98011-8805, USA).
P8: *P. chrysogenum* strain (available from Panlabs)
Materials:
LCS Agar slants: (J. Lein, "The Panlabs penicillin strain improvement program" p. 105–139 in Vanek, Z. and Hostalek, Z. (eds.) Overproduction of microbial metabolites, strain improvement and process control strategies. Butterworth, Boston (1986)) LCS medium: Lactose monohydrate 1.5%, corn steep liquor 0.5% peptone 0.5%, NaCl 0.4%, $MgSO_4.7H_2O$ 0.05%, $KH_2PO_4$ 0.06%, $FeCl_3.6H_2O$ 0.0005%.
Tween®-80: Merck Art. 822187
P-1 Seed Medium: (J. Lein, supra, (1986))
P-2 Fermentation Medium: (J. Lein, supra, (1986))
Vector:
pUCl9: 2.6 kb Asp719-SalI fragment
Transformation selective marker:
*E. coli* Tn5 phleomycin resistant gene expressed by *Aspergillus oryzae* TPI (triose phosphate isomerase) promoter and *Aspergillus niger* AMG (amyloglucosidase) terminator.
Equipment:
Sepharose® S FF column (Pharmacia Biotech)
Phenyl-Sepharose CL 4B column (150 ml) (Pharmacia Biotech)
PD10 column (Pharmacia Biotech)
Supelcosil RP C-18 I)B column (250×4.6 mm) supelguard (Supelco)
Flow-one/Beta serie 100 radioactivity detector (Radiomatic)
Yttrium silicate flow cell (Radiomatic)
Sephacryl S-200 column (181 ml) (Pharmacia Biotech)
Chromatofocussing PBE™ 94 column (20 ml) (Pharmacia Biotech)
Pharmacia LKB PhastSystem (Pharmacia Biotech)
Cibacron Blue 3GA column (Sigma)
ABI 1000S photodiode array HPLC-detector (Applied Biosystems)
HPLC (Waters)
Applied Biosystems 394 DNA/RNA synthesizer
Applied Biosystems 473 Amino Acid sequencer
Waters™ 991 Photodiode Array Detector
Reference enzymes and compounds:
Acetyl-coenzyme A Sigma)
Acetyl-coenzyme A synthetase (Sigma)
Bovine serum albumin ("BSA") (Sigma A7638)

Gelfiltration Calibration Kit (Pharmacia Biotech)

Phenoxyacetic acid coenzyme A ester (M. J. Alonso et al., J. Antibiot., 41, p. 1074–1084, 1988)

Phenylacetic acid coenzyme A ester (Sigma)

Adipic acid coenzyme A ester was prepared as follows: Adipoyl chloride (0.14 ml; Aldrich) was added to a well-stirred and ice-water cooled suspension of coenzyme A—Na salt (400 mg; $5.152 \times 10^{-4}$ mmol. Sigma) in acetone (60 ml; Merck PA) +water (0.6 ml)+0.2M $KHCO_3$ (to raise the pH to >7) under an atmosphere of nitrogen. The pH of the reaction contents were brought to about 7.7 and, then, further stirred for about 60 min at the same temperature. Thereafter, acetone was removed partially under reduced pressure, the resulting product dissolved in cold water and freeze dried. Yield 0.0890 g. Finally the product was subjected to Ultrafiltration.

Buffers:

Buffer A: 50 mM Tris/HCl, pH 8.5, 1.36M ammonium sulphate, 4 mM EDTA, 5 mM ATP, 5 mM ascorbic acid, 1 mM PMSF (phenyl-methyl-sulfonyl-fluoride).

Buffer B: 50 mM Tris/HCl, pH 8.5, 0.68M ammonium sulphate, 4 mM EDTA, 5 mM ATP, 5 mM ascorbic acid, 1 mM PMSF.

Buffer C: 50 mM Tris/HCl, pH 8.5, 20% glycerol, 4 mM EDTA, 5 mM ATP, 5 mM $MgCl_2$, 5 mM ascorbic acid, 1 mM PMSF.

Buffer D: As buffer C, 150 mM KCl.

Buffer E: 10 mM Tris/HCl, 20% glycerol, 4 mM EDTA, 5 mM $MgCl_2$, 5 mM ATP, 5 mM ascorbic acid and 1 mM PMSF, pH 8.2.

Buffer F: 50 mM Tris/HCl, 20% glycerol, 4 mM EDTA, 5 mM $MgCl_2$, 5 mM ATP and 5 mM ascorbic acid, pH 7.5.

Solutions:

Solution A: 50 mM Tris/HCl, pH 8.5; 35% ammonium sulphate, 4 mM EDTA, 5 mM ATP, 1 mM PMSF, 5 mM mercaptoethanol.

Solution B: 10 µl of 0.25 M $MgCl_2$, 50 µl of 0.1 M ATP in 50 mM Tris/HCl, pH 8.0, 50 µl of 20 mM CoASH in 50 mM Tris/HCl, pH 8.0 and 30 µl of 0.2 M phenoxyacetic acid or phenylacetic acid or adipic acid or hexanoic acid in 50 mM Tris/HCl, pH 8.0 mixed and equilibrated at 25° C. for 5 minutes.

Solution C: 50 mM Tris/HCl, pH 8.5, ammonium sulphate (20% saturation), 4 mM EDTA, 5 mM ATP, 5 mM ascorbic acid, 1 mM PMSF, 4 mM $MgCl_2$.

Solution D: 5 ml contains 1.2 M $MgSO_4$, 10 mM $NaH_2PO_4$, pH 5.8, 150 mg Novozym234 (batch #1199), 100 µl chitinase (Sigma, 4 U/ml).

Solution E: 0.6M sorbitol, 100 mM Tris-HCl, pH 7.0

Solution F: 1.2M sorbitol, 10 mM Tris-HCl, pH 7.5, 10 mM $CaCl_2$.

Solution G: 60% PEG4000(BDH#29576), 10 mM Tris-HCl, pH 7.5, 10 mM $CaCl_2$.

Solvent H: 20% (v/v) acetonitrile in 25 mM sodiumphosphate buffer, pH 6.5.

Solvent I: 13% methanol in 20 mM sodium phosphate, pH 2.5

Substrate solution A: 100 µl of 0.25M $MgCl_2$, 500 µl of 0.1M ATP in 50 mM Tris/HCl, 500 µl of 20 mM CoASH in 50 mM Tris/HCl, and 300 Ml of 0.067M potassium acetate in 50 mM Tris/HCl.

Solvent A: 15% (v/v) acetonitrile in 25 mM sodium phosphate buffer, pH 6.5.

Solvent B: 5% (v/v) acetonitrile in 25 mM sodium phosphate buffer pH 6.5

Methods:

A) Cloning of the phenoxyacetyl-coenzyme A synthetase from *P. chrysogenum*

Genomic DNA from *P. chrysogenum* is isolated according to the procedure of Schwarz-Sommer et al. (EMBO J., 3, p. 1021–1028, 1984) and partially digested with Sau3A. Fragments 15–23 kb in size are then isolated and ligated to lambda EMBL3 BamHI arms (Promega).

When purified to homogeneity, a partial amino acid sequence of the phenoxyacetyl-coenzyme A synthetase can be determined by applying an Edman degradation to the ligase or a fragment thereof using an Applied Biosystems 473 Amino Acid Sequencer. From the amino acid sequence degenerated primers can be prepared by the i phosphoamidite method described by Beaucage and Caruthers, Tetrahedron Letters, 22, p. 1859–1869, 1981, e.g. by using an Applied Biosystems 394 DNA/RNA synthesizer.

By screening of the genomic library of *P. chrysogenum* DNA constructed in lambda EMBL3 with plaque hybridization method (Maniatis et al., 1982, Molecular cloning: A laboratory manual, Cold Spring Harbor Laboratory, New York) a clone can be isolated, which hybridises with the degenerated primer specific for the phenoxyacetyl-coenzyme A synthetase gene.

The region of the lambda clone containing the functional phenoxy-acetyl-coenzyme A synthetase gene is subcloned into the pUC19 vector together with the Tn5 phleomycin resistant gene, and the resulting plasmid can be used for the transformation of e.g. *P. chrysogenum*.

B) Transformation of *P. chrysogenum*

*Penicillium chrysogenum* strain B10 (high yielding strain) is cultured in 2 flasks of 100 ml LCS medium for 36 hrs. at 26° C. Mycelia is collected on Myra cloth and washed thoroughly with 500 ml 0.6M $MgSO_4$, Mycelia is then placed into a plastic tube and suspended in 5 ml Solution D and placed on ice for 5 min. 750 µl BSA (12 mg/ml) is added to the mycelial suspension and further incubated at 30° C. for 1 to 2 hours with gentle shaking. Protoplast formation is controlled with light microscope.

Protoplasts are collected on Myra-cloth and layered carefully over 5 ml of Solution E. After centrifugation slowly up to 2000 rpm for 15 min., protoplasts localized at the interphase between Solution E and Solution D are taken by pipeting and diluted by adding 2 vol. of Solution F and again centrifuged at 2500 rpm for 5 min. Protoplast pellet is washed twice with Solution F and isolated protoplasts are diluted by adding Solution F to get $1-2 \times 10^7$ cells/ml. 100 µl of protoplasts is used for a transformation.

10 µg DNA prepared by CsCl density gradient (Maniatis et al., 1982, supra) is added to the protoplasts and left at room temperature for 20 min. Then 200 µl of Solution G are added and left at room temperature for 20 min. 3 vol. of 1.2 M sorbitol is then added and protoplast-DNA aggregate is centrifuged at 2500 rpm for 10 min. The pellet is then resuspended by adding 300 µl 1.2 M sorbitol and plated on 3 selective plates (100 µl each) containing 50 µg/ml phleomycin in the LCS slant agar. Plates are incubated at 26° C. until transformants appear.

The transformants can then be isolated and tested for their penicillin producing capacity by fermentation in shake flasks.

C) Fermentation of *P. chrysogenum*

Lyophilized spores of *Penicillium chrysogenum* strain B10 or P8 (Panlabs) were inoculated on 10 ml LCS Agar slants after suspension in distilled water containing 0.1% (v/v) of Tween®-80. After incubation at 25° C. for 10 days, the spores from each slant surface were suspended in 10 ml of 0.1% Tween®-80 and 5 ml portion of this suspension was used to inoculate 50 ml of P-1 Seed Medium in 300 ml Erlenmeyer flasks. The seed cultures were incubated at 25° C. on a rotary shaker at 290 rpm. After 48 hours, 2 ml aliquots of seed culture were used for inoculation of the P-2 fermentation medium, 35 ml in 300 ml Erlenmeyer flasks (lard oil replaced by olive oil). The cultures were incubated at 25° C. at 290 rpm until harvested.

D) Harvest, extraction and precipitation

The cells from a 3 days old culture of *P. chrysogenum* were isolated by filtration and quickly washed with 5 volumes of 0.9% sodium chloride. The cells were frozen in liquid nitrogen and homogenized in a mortar. The enzyme was extracted by suspension in Solution A. Cell debris was removed by centrifugation. The extract was brought to 50% ammonium sulphate saturation and the precipitate was removed by centrifugation. The enzyme could then be precipitated by addition of ammonium sulphate to 70% saturation. After centrifugation the pellet was dissolved in Solution C.

E) Phenyl-Sepharose® CL 4B column chromatography 2280 mg of protein (95 ml) (from the previous section) was applied to a Phenyl-Sepharose CL 4B column (150 ml), equilibrated in Buffer A, flow rate: 60 ml per hour. The column was washed with 500 ml of buffer A, followed by a gradient from 100% Buffer B to 100% Buffer C, total volume 1800 ml. Fractions of 8 ml were collected.

All fractions were analyzed for phenoxyacetyl-coenzyme A synthetase activity and acetyl-coenzyme A synthetase activity. The phenoxyacetyl-coenzyme A synthetase activity eluted between the fractions Nos. 115–277, showing a peak of activity in fraction No. 175. An acetyl-coenzyme A synthetase activity eluted between the fractions Nos. 108–157, showing a peak of activity in fraction No. 118.

F) Cibacron Blue column chromatography

Fractions Nos. 143–225 from the Phenyl-Sepharose chromatography were pooled and the protein precipitated by addition of ammonium-sulphate to 65% saturation. The precipitate was resuspended in 10 ml of Buffer C and desalted using a PD10 column. Final sample volume: 16 ml.

The sample was applied to a column packed with 20 ml of Cibacron Blue equilibrated with buffer C. The column was washed with 10 column volumes of Buffer C and eluted with a KCl gradient (0–0.25 M KCl) using a flow rate of 25 ml per hour. The eluate was collected as fractions of 8.3 ml. The phenoxyacetyl-coenzyme A synthetase activity eluted between fractions No. 36 and No. 65 with a maximum in fraction No. 45.

G) Gel filtration S-200 (Surer fine)

Fractions Nos. 36–56 from the Cibacron Blue chromatography were pooled and concentrated by ultra filtration (cut off 10.000), desalted on a PD10 column to Buffer D and 7 mg protein (3.3 ml) was applied to a Sephacryl S-200 column (181 ml) equilibrated with the same buffer. The column was eluted with Buffer D (flow rate 10 ml per hour) and aliquots of 1 ml were collected and assayed. The phenoxyacetyl-coenzyme A synthetase eluted in the fractions 72 to 118, showing a peak of activity in fraction 87.

H) Chromatofocusing PBE™ 94

Fractions Nos. 79–107 were pooled, concentrated by ultra filtration (cut off 10.000) and desalted on a PD10 column using Buffer E. Final sample volume: 3.0 ml.

The sample was applied to a 20 ml PBE™ 94 column equilibrated in Buffer B and the column was eluted with buffer E using a flow of 30 ml per hour. Fractions of 1.5 ml were collected. The phenoxyacetyl-coenzyme A synthetase activity eluted in fractions Nos. 11–40, maximum activity obtained in fraction No. 17.

I) Sepharose® S FF column chromatography

The protein (149 mg) in an aliquot from the pooled fractions no. 143–225 from the Phenyl-Sepharose chromatography (see above) was precipitated by addition of ammonium sulphate to 65% saturation. The precipitate was resuspended in Buffer F and desalted using a PD10 column. Final sample volume: 28 ml.

The sample was applied to a 50 ml Sepharose S FF column equilibrated in Buffer F. After sample application the column was washed with 150 ml Buffer F and eluted with a KCl gradient (0–0.3 M KCl). A flow rate of 50 ml per hour and a fraction size of 5 ml was used at all steps. The phenoxyacetyl-Coenzyme A synthetase activity eluted between fractions 45 and 120 with a maximum in fraction no. 48, while the major protein peak appeared in fraction no. 16.

J) Direct assay for phenoxyacetyl-coenzyme A synthetase and phenylacetyl-coenzyme A synthetase The reaction was started by addition of 100 $\mu$l of enzyme solution to Solution B containing phenoxyacetic acid (or phenylacetic acid) and CoASH. After incubation for 30 minutes at 25° C. the reaction was stopped by addition of 240 $\mu$l of 0.5% trifluoroacetic acid. The precipitate formed was removed by centrifugation and the amount of phenoxyacetic acid coenzyme A ester (or phenylacetic acid coenzyme A ester) formed was analyzed by HPLC.

Detection of phenoxyacetic acid coenzyme A ester or phenylacetic acid coenzyme A ester by HPLC:
Column: Supelcosil RP C-18 DB with Supelguard
Detection: UV-Detection at 260 nm
Solvent A: 15% (v/v) acetonitrile in 25 mM sodium phosphate buffer, pH 6.5.
Flow: 1 ml/min
Retention time for phenoxyacetic acid coenzyme A ester: 9.7 minutes and 9.0 minutes for phenylacetic acid coenzyme A ester. Phenoxyacetic acid coenzyme A ester and phenylacetyl-coenzyme A ester was quantized relatively to a standard.

K) Direct assay for adipoyl-coenzyme A synthetase

The reaction was started by addition of 1 volume of enzyme to 1.4 volumes of solution B containing adipic acid, adjusted to pH 8.5. A typical incubation mixture consisted in 250 $\mu$l enzyme and 350 $\mu$l solution-B. Incubation was at 30° C. At regular time intervals samples were withdrawn from the incubation mixture and mixed with an equal part of 0.5% trifluoroacetic acid. The precipitate formed was removed by centrifugation. The amount of adipoyl-coenzyme A ester formed was analyzed by HPLC.

Detection of adipoyl-coenzyme A ester by HPLC:
Column: Supelcosil RP C-18-DB
Detection: UV-detection at 257 nm
Eluent: 5% Actonitrile in 25 mM sodium phosphate buffer pH 5.6
Flow: 1 ml/min
Retention time for adipoyl-coenzyme A ester: 11.4 minutes.
Adipoyl-coenzyme A ester was used as reference.

L) Direct assay for hexanoyl-coenzyme A synthetase

The reaction was started by addition of 1 volume of enzyme to 1.4 volumes of solution B containing hexanoic acid, adjusted to pH 8.5. A typical incubation mixture consisted in 250 $\mu$l enzyme and 350 $\mu$l solution B. Incubation was at 30° C. At regular time intervals samples were withdrawn from the incubaiton mixture and mixed with an equal part of 0.5% trifluoroacetic acid. The precipitate formed was removed by centrifugation. The amount of hexanoyl-coenzyme A ester formed was analyzed by HPLC.

Detection of hexanoyl-coenzyme A ester by HPLC:
Column: Supelcosil RP C-18-DB
Detection: UV-detection at 257 nm
Eluent: 15% Acetonitrile in 25 mM sodium phosphate buffer pH 6.5
Flow: 1 ml/min
Retention time for hexanoyl-coenzyme A ester: 20.4 minutes.

M) Direct assay for acetyl-coenzyme A synthetase

Substrate solution A was mixed and pH was adjusted to 8.0 with 4M KOH. 40 µl of acetic acid-1-$^{14}$C, sodium salt, (41.8 mCi/mmol, 1.0 mCi/ml) was added and the mixture was equilibrated at 35° C. Assay: 25 µl of enzyme and 35 µl of substrate solution A was mixed and incubated at 35° C. for 30 minutes. The reaction was stopped by addition of 60 µl of 0.5% trifluoroacetic acid. Any precipitate formed was removed by centrifugation and amount of acetyl-coenzyme A ester formed was analyzed by HPLC supplied with a radioactivity detector. Non-radioactive compounds were detected by UV detection at 210 nm placed in series with the Radiomatic detector.

Detection of acetyl-coenzyme A ester by HPLC:
Column: Supelcosil RP C-18 DB column with Supelguard
Detection: Radioactive compounds were detected using a
  Flowone/Beta serie 100 radioactivity detector (Radiomatic) equipped with a 250 µl yttrium silicate flow cell.
  UV-detection at 210 nm
Solvent B: 5% (v/v) acetonitrile in 25 mM sodiumphosphate buffer pH 6.5
Flow: 1 ml/min
Retention time for acetyl-coenzyme A ester: 6.9 minutes As standard was used acetyl-coenzyme A (Sigma) as well as incubation of the substrate mixture A with acetyl-coenzyme A synthetase (Sigma) followed by analysis of the formed $^{14}$C-acetyl-coenzyme A by HPLC.

N) Detection of penicillin V and penicillin G by HPLC

After the incubation the vial was placed on ice for 10 minutes. After centrifugation the supernatant was analyzed by HPLC for penicillin V or penicillin G using the following conditions:
Column: Supelcosil LC C-18 DB column (250×4.6 mm) with Supelcoguard
Detection: UV-detection at 215 Dm.
Solvent: Solvent H
Flow: 1 ml/min
Injection volume: 10 µl
Retention time (RT) for penicillin V was 13.3 minutes and 8.7 minutes for penicillin G.

O) Sample preparation for HPLC determination of-ACV and IPNS

A sample of 2 ml was drawn from the shake flask and quickly cooled to 0–4° C., diluted 25 times with 25 mM sodium phosphate, pH 6.5 and ultrafiltered (cut off 10,000). Dithiothreitol (DTT) was added to the filtrate to a final concentration of 5 mM and the samples analyzed by HPLC.
Column: Supelcosil LC-18 DB column (250×4.6 mm) with Supelguard.
Detection: UV-detection at 210 nm
Solvent: Solvent I
Flow: 2 ml/min
Temperature: 35° C.
Injection volume: 10 µl
Retention times (RT) for isopenicillin N and ACV: 5.7 and 17 minutes, respectively.

P) Extraction of acyl-coenzyme A from P. chrysogenum

Acyl-coenzyme A compounds from P. chrysogenum were extracted following the method of Barbera E. Corkey and Jude T. Deeney "Acyl CoA regulation of metabolism and signal transduction" Progress in clinical and Biological Research, 321, p. 217–232, 1990.

P. chrysogenum (strain B10 or strain P8) was grown in shake flasks as described in the section "A) Fermentation of P. chrysogenum". After 4 days of growth in P-2 medium (pH 6.1), the cells were quickly cooled in a salt-ice bath and centrifugated for 30 seconds at 22000 $g_{av}$ and the pellet was frozen in liquid nitrogen within 3 minutes after cell harvest. The cells were thawed after addition of two volumes of 0.6 N trichloroacetic acid. After sonication for 30 seconds the cell extracts were isolated by centrifugation (12000 $g_{av}$ for 30 seconds). The trichloroacetic acid was removed by extraction with diethyl ether until the pH in the aqueous phase was 6. The aqueous phase (containing the acyl-coenzyme A compounds) was lyophilized and the sample was finally dissolved in 25 mM sodium phosphate buffer pH 6.5 and analyzed by HPLC using the conditions given under "Detection of phenoxyacetic acid coenzyme A".

Q) Labelling of phenoxyacetic acid Metabolites in P. chrysogenum

P. chrysogenum (B10 or P8) was grown in shake flasks as described in the section "Fermentation of P. chrysogenum". After 4 days of growth in P-2 medium (pH 6.1) 10 ml of cells were transferred to a 50 ml Erlenmeyer flask containing 250 µl 1-$^{14}$C)-phenoxyacetic acid (72 µCi/ml, 9,7 µCi/µmole). The flask was then incubated at 26° C. while shaking.

After 1, 15, 30, 60, 120, 240 and 360 minutes 1 ml cells were removed, immediately cooled to 0° C. and centrifugated for 1 minute at 22000 $g_{av}$. The pellet was suspended in 500 µl 5% phosphoric acid and 500 µl methanol and the mixture was sonicated for 1 minute. After centrifugation the supernatant was analyzed by HPLC using a radioactivity detector for identification of labelled metabolites.

HPLC conditions:
Column: Supelcosil LC-18 DB column (250×4.6 mm) with Supelguard
Detection: Radiomatic A-140 with a yttrium silicate flow cell
Solvent 1: 25 mM sodium phosphate, pH 6.5
Solvent 2: acetonitrile
Gradient

| time (min.) | solvent 1 (%) | solvent 2 (%) |
|---|---|---|
| 0 | 100 | 0 |
| 40 | 70 | 30 |
| 45 | 70 | 30 |
| 46 | 100 | 0 |
| 60 | 100 | 0 |

Flow: 1 ml/min.

The only peaks that appeared in the chromatogram corresponded to phenoxyacetic acid (RT: 14.5 min.), p-hydroxy-phenoxyacetic acid (RT: 8.4 min) and penicillin V (RT: 34 min.). The peaks for p-hydroxy-phenoxyacetic acid and penicillin V were only detectable after incubation for 60 minutes.

EXAMPLES

Example 1

Ligase activity in a high and low yielding strain of P. chrysogenum

The yields of penicillin when fermenting P. chrysogenum strain P8 are generally considered low to intermediate, while P. chrysogenum strain B10 is considered a high yielding strain.

The strains of *P. chrysogenum* (B10 and P8) were fermented as describes in the section "Fermentation of *P. chrysogenum*". The cells were harvested and the phenoxyacetyl-coenzyme A synthetase extracted as described in the section "B) Harvest, extraction and precipitation", and the activity of phenoxyacetyl-coenzyme A synthetase (ligase) in the two extracts were determined as described in the section "Direct assay for phenoxyacetyl-coenzyme A synthetase and phenylacetyl-coenzyme A synthetase".

The results of the phenoxyacetyl-coenzyme A synthetase activity determinations are shown in the table below.

TABLE 1

| P. chrysogenum strain | relative phenoxy-acetyl-coenzyme A synthetase activity (%) | relative penicillin V produced (%) |
| --- | --- | --- |
| P8 | 27.5 | 40 |
| B10 | 100 | 100 |

This example clearly shows that the activity of phenoxyacetyl-coenzyme A synthetase is correlated with the penicillin production by the strain.

Example 2
Accumulation of intermediate metabolites

*P. chrysogenum* (B10) was grown in shake flasks as described in the section "A) Fermentation of *P. chrysogenum*". After inoculation into the P-2 fermentation medium, the concentrations of ACV and isopenicillin N in the culture broth were determined by HPLC each day for 7 days, using the procedure described above.

The concentrations of ACV and isopenicillin N as a function of the fermentation time are given in FIG. 1.

The figure clearly demonstrates an accumulation of ACV and isopenicillin N in the culture broth from a *P. chrysogenum* fermentation.

Example 3
In vitro synthesis of penicillin V and penicillin G

A mixture of 25 µl 60 th phenoxyacetic acid*, 25 Jul 40 M ATP*, 25 µl 6 mM coenzyme A*, and 10 µl 6 mM 6-aminopenicillanic acid* was incubated at 30° C. in the presence of 10 µl phenoxyacetyl-coenzyme A synthetase (from the pooled fractions no. 11–40 from the Chromatofocusing PBE™ 94 chromatography (described above)) and 10 µl acyl-coenzyme A: 6-aminopenicillanic acid acyltransferase (purified from *P. chrysogenum* as described by Emilio Alvarez et al. in "Purification to Homogeneity and Characterization of Acyl-Coenzyme A:6-Aminopenicillanic Acid Acyltransferase of *Penicillium Chrysogenum*" Antimicrobial Agents and Chemotherapy, 31(11), p. 1675–1682, 1987. (*: dissolved in 50 mM Tris/HCl, pH 7.8, 10 MM $MgCl_2$ and 5 av ascorbic acid)

For the in vitro synthesis of penicillin G the phenoxyacetic acid was replaced by 25 µl 60 mM phenylacetic acid.

After 15 minutes the incubation was stopped by addition of 100 µl methanol and the vial placed on ice for 10 minutes. After centrifugation the supernatant was analyzed by HPLC for penicillin V or penicillin G as described above.

Identification of the penicillin V or penicillin G

Identification of the penicillin V or penicillin G peaks in the chromatogram were verified by spiking with standard solutions of penicillin V and penicillin G, respectively, and by comparing the UV spectrum at the peak inflection points and apex with the spectrum from the two penicillin standards using a ABI 1000S photodiode array HPLC-detector as described above.

When either coenzyme A, 6-aminopenicillanic acid, ATP or the phenoxyacetic acid or phenylacetic acid was omitted from the reaction mixture no penicillin V or G was synthesized.

This confirms that the isolated enzyme exhibits phenoxyacetyl-coenzyme A activity and phenylacetic acid coenzyme A activity (ligase activity).

Example 4
In vitro synthesis of V-DCA

A mixture of 25 µl phenoxyacetic acid*, 25 µl 40 mM ATP*, 25 µl 6 mM coenzyme A*, and 10 µl 7-aminodesacetoxycephalosporanic acid* (7-ADCA) is incubated at 30° C. in the presence of 10 µl phenoxyacetyl-coenzyme A synthetase (from the pooled fractions no. 11–40 from the Chromatofocusing PBE™ chromatography (described above) and 10 µl Acyltransferase (purified from *P. chrysogenum* as described by Emilio Alvarez in "Purification to Homogeneity and Characterization of Acyl-Coenzyme A:6-Aminopenicillanic Acid Acyltransferase of *Penicillium Chrysogenum*" Antimicrobial Agents and Chemotherapy, 31(11), p. 1675–1682, 1987).
(*: dissolved in 50 mM Tris/HCl, pH 8.0, 10 MM $MgCl_2$ and 5 mM Ascorbic Acid)

After 15 minutes the incubation was stopped by addition of 100 µl 0.5% trifluoroacetic acid and the vial placed on ice for 10 minutes. After centrifugation the supernatant was analyzed by HPLC for V-DCA using the chromatographic conditions described in the section "O) Labelling of phenoxyacetic acid metabolites in *P. chrysogenum*". Retention time for V-DCA: 32 minutes.
Identification of V-DCA The identification of the V-DCA peak in the chromatogram was verified by spiking with standard solutions of V-DCA and by comparing the UV spectrum at the peak apex with the spectrum from the V-DCA standard using a Waters™ 991 Photodiode Array Detector.

Example 5
Determination of molecular weight by gel-filtration

The molecular weight of the phenoxyacetyl-coenzyme A synthetase (ligase) was determined by comparing the elution volume from the gel filtration described in the section "Gel filtration S-200 (super fine)" with the elution volumes for applied standards from the gel filtration Calibration Kit (Ribonuclease A (13,700 Dalton), Chymotrypsinogen A (25,000 Dalton), Ovalbumin (43,000 Dalton), Bovine serum albumin (67,000 Dalton) and Aldolase (158,000 Dalton) on the same column, and using the same conditions as given above, the phenoxyacetyl-coenzyme A synthetase has an apparent molecular weight of about 50,000 Dalton.

Example 6
Isoelectric point (pI)

The isoelectric point (pI) was estimated by changing the pH in the Buffer F (pH 7.5) used in Sepharose S FF column chromatography (described above) to 8.5. Keeping the other parameters constant, it was found that. the phenoxyacetyl-coenzyme A synthetase (ligase) was not retained on the column during the elution with buffer F (pH adjusted to 8.5).

This indicates that the pH where the net charge of the enzyme is zero (i.e. the isoelectric point) is above 7.25.

Example 7
Phenoxyacetyl-coenzyme A in extracts

To get an indication of the presence of phenoxyacetyl-coenzyme A synthetase (ligase) activity, acyl-coenzyme A was extracted as described in the section "Extraction of acyl-coenzyme A from *P. chrysogenum*" and analyzed by HPLC.

Even though the detection limit in the HPLC-assay was below 50 pmol, no phenoxyacetic acid coenzyme A could be identified in the cell extracts. Neither did extraction of labelled phenoxyacetic acid metabolites show any detectable phenoxyacetic acid coenzyme A in cell extracts as described in the section "Labelling of phenoxyacetic acid metabolites in *P. chrysogenum*".

Example 8

Characterization

Phenoxyacetyl-coenzyme A synthetase (ligase) from the purification (described above) was used for the further characterization of the enzyme.

Temperature and DH-optimum

The phenoxyacetyl-coenzyme A synthetase was assayed, as described in the section "Direct assay for phenoxy-coenzyme A synthetase", using temperatures from 15–50° C. and varying the pH-values in the assay from 6.5 to 9.0.

Figure 2:
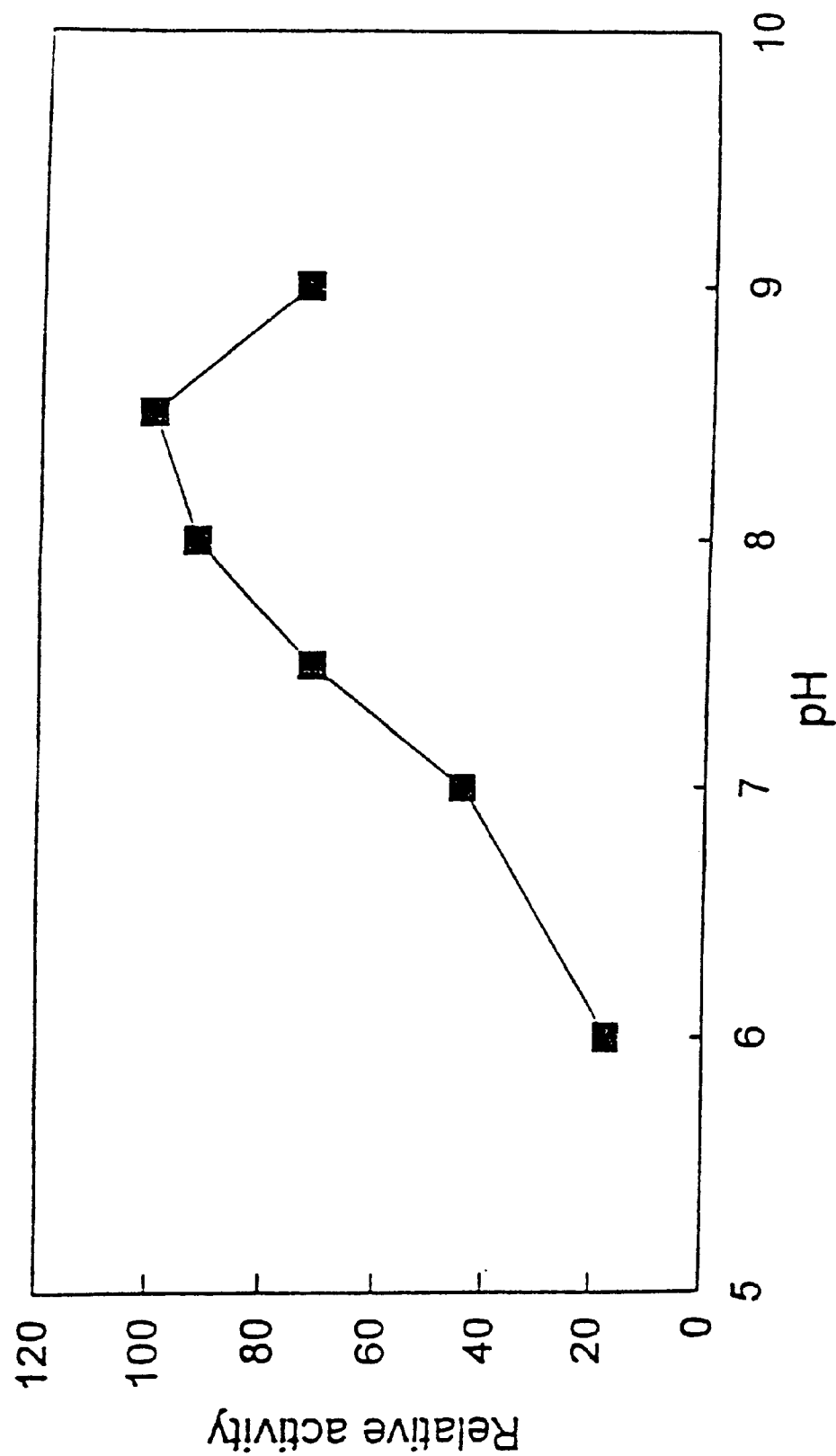
FIG. 2 shows the pH-optimum for ligase activity.
Figure 3:
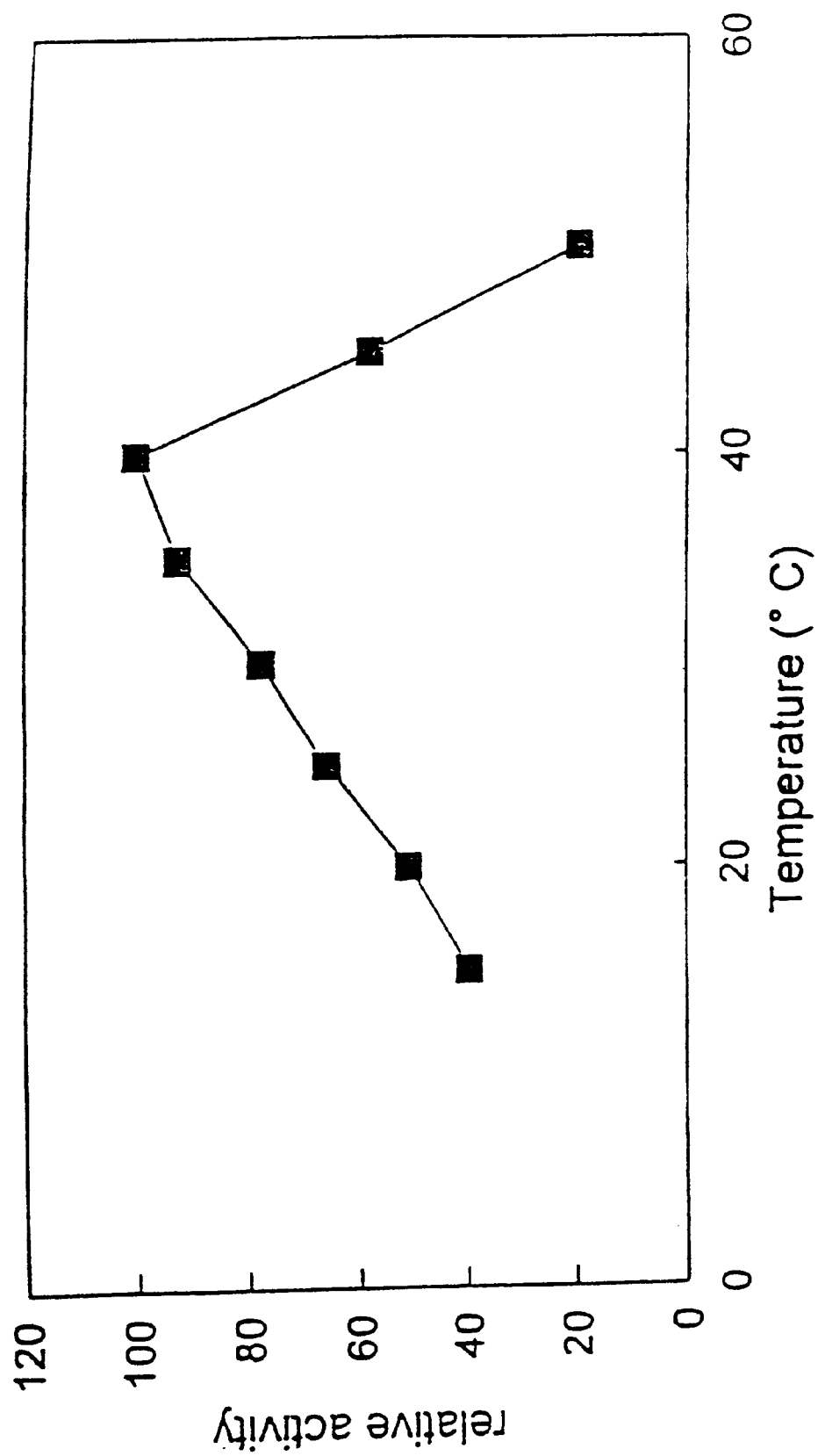
FIG. 3 shows the temperature optimum for ligase activity.

As shown in FIG. 2, the phenoxyacetyl-coenzyme A synthetase activity reached a maximum around pH 8–8.5, and FIG. 3 shows a temperature optimum of around 40° C.

Substrate specificity

Incubating the phenoxyacetyl-coenzyme A synthetase with phenoxyacetic acid, phenylacetic acid, adipic acid, hexanoic acid and acetic acid, using the assay conditions given in the section "Direct assay for phenoxyacetyl-coenzyme A synthetase", in the section "Direct assay for acetyl-coenzyme A synthetase", in the section "Direct assay for adipoyl-coenzyme A synthetase" and in the section "Direct assay for hexanoyl-coenzyme A synthetase", the following results were obtained:

| substrate | relative activity |
|---|---|
| phenoxyacetic acid | 100 |
| phenylacetic acid | 80 |
| adipic acid | 19 |
| hexanoic acid | 320 |
| acetic acid | <1 |

Determination of the apparent $K_M$ for ATP, phenoxyacetic acid, coenzyme A, and MaCl$_2$ The activity of phenoxyacetyl-coenzyme-A synthetase was assayed as described in the section "Direct assay for phenoxyacetyl-coenzyme A synthetase", in the presence of varying concentrations of the substrates, one at the time. The apparent $K_M$-values (at the conditions used in this assay) were determined from Eadie-Hofstee, Hanes and Lineweaver-Burk plots, as described by Nicholas C. Price & Lewis Stenens in "Fundamentals of Enzymology", Oxford University Press, p. 123, 1982. From the plots it was clear that the phenoxyacetyl-coenzyme A synthetase obeyed Michaelis-Menten kinetics with respect to the individual substrates.

The results are displayed in the Table 2 below.

TABLE 2

| | Concentrations mM | $K_M$ mM |
|---|---|---|
| Phenoxyacetic acid | 0–40 | 3.2 |
| ATP | 0–10 | 0.22 |

TABLE 2-continued

| | Concentrations mM | $K_M$ mM |
|---|---|---|
| coenzyme A | 0–4.0 | 0.57 |
| MgCl$_2$ | 0–15 | 1.6 |

$K_M$ is the Michaelis constant

Inhibition of phenoxyacetyl-coenzyme A synthetase from phenylacetic acid and acetic acid The activity of phenoxyacetyl-coenzyme A synthetase was assayed as described in the section "Direct assay for phenoxyacetyl-coenzyme A synthetase", in the presence of varying concentrations of either phenylacetic acid or acetic acid at various concentrations of phenoxyacetic acid.

The concentrations of the phenoxyacetic acid used in the assay were 1.7; 3.3; 6.6; 20 and 42 mM and the concentration of phenylacetic acid and acetic acid were 0; 1.0; 5.0; 10 and 25 mM, respectively.

From Lineweaver-Burk plots it was demonstrated that phenylacetic acid acted as a competitive inhibitor for the phenoxyacetyl-coenzyme A synthetase, whereas the acetic acid did not act as a competitive inhibitor for the phenoxyacetyl-coenzyme A synthetase at the assay conditions used.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. An isolated acyl-coenzyme A synthetase obtained from a filamentous fungus selected from the group consisting of *Penicillium chrysogenum, Aspergillus nidulans*, and *Cephalosporium acremonium* which, in the synthesis of the corresponding acyl-coenzyme A esters, is at least 10 times more active towards phenoxyacetic acid than towards acetic acid, and is at least 10 times more active toward phenylacetic acid than towards acetic acid, wherein said synthetase comprises a property selected from the group consisting of (a) an apparent molecular weight of between 40,000 and 60,000 Daltons as determined by gel filtration, (b) an apparent activity optimum in the range of pH 7.0–9.0, and (c) an apparent activity optimum in the temperature range of 35–45° C.

2. The synthetase according to claim 1 which is at least 10 times more active towards adipic acid than towards acetic acid.

3. The synthetase according to claim 1 which is at least 10 times more active towards hexanoic acid than towards acetic acid.

4. The synthetase according to claim 1, characterized by having an apparent molecular weight of about 50,000 Daltons, as determined by gel filtration.

5. The synthetase according to claim 1, characterized by having an apparent activity optimum in the range of pH 8.0–8.5.

6. The synthetase according to claim 1, characterized by having an apparent activity optimum at a temperature of about 40° C.

7. The synthetase according to claim 1, characterized by being immunologically reactive with an antibody raised against said purified synthetase from *P. chrysogenum* strain B10.

8. A DNA construct comprising a DNA sequence encoding a synthetase according to claim 1, wherein said DNA sequence is obtained from a filamentous fungus selected from the group consisting of *Penicillin chrysogenum, Aspergillus nidulans,* and *Cephalosporium acremonium.*

9. A recombinant vector or transformation vehicle comprising the DNA construct according to claim 8.

10. The vector or transformation vehicle according to claim 9, wherein said DNA sequence encoding the synthetase is operably linked to a promoter sequence and optionally to a terminator sequence.

11. The vector or transformation vehicle according to claim 10, wherein said promoter sequence is from a gene involved in the biosynthesis of β-lactams that is different than the gene encoding the synthetase.

12. The vector or transformation vehicle according to claim 9, wherein said DNA construct is operably linked to a sequence encoding a targeting signal or secretion signal.

13. A microbial host cell comprising a DNA construct according to claim 8.

14. A microbial host cell comprising a vector or transformation vehicle according to claims 9.

15. The microbial host cell according to claim 13, which is a bacterial or a fungal host cell.

16. The microbial host cell according to claim 14, which is a bacterial or fungal host cell.

17. A process for the production of a β-lactam antibiotic comprising:

i) fermentation of a microorganism capable of producing said β-lactam antibiotic which is transformed with a DNA construct according to claim 8, and ii) recovering said β-lactam antibiotic.

18. A process for the production of a β-lactam antibiotic comprising:

i) fermentation of a microorganism capable of producing said β-lactam antibiotic which is transformed with a vector or transformation vehicle according to claim 9, and ii) recovering said β-lactam antibiotic.

19. The process according to claim 17, wherein the transformed microorganism is selected from the group consisting of Penicillin, Cephalosporium, Aspergillus, Nocardia, Streptomyces, Bacillus, Cerospora, Microspora, other Eubacteria, other Actinomycetes and filamentous fungi.

20. The process according to claim 18, wherein the transformed microorganism is selected from the group consisting of Penicillin, Cephalosporium, Aspergillus, Nocardia, Streptomyces, Bacillus, Cerospora, Microspora, other Eubacteria, other Actinomycetes and filamentous fungi.

21. A method for the production of a β-lactam antibiotic comprising incubating a carboxylic acid, coenzyme A, a synthetase exhibiting ligase activity according to claim 1, acyltransferase and a β-lactam intermediate.

22. The method according to claim 21, wherein the β-lactam intermediate is selected from the group consisting of isopenicillin N (IPN), 6-aminopenicillanic acid (6-APA), 7-aminocephalosporanic acid (7-ACA), 7-aminodesacetoxycephalosporanic acid (7-ADCA) and 7-aminodeacetylcephalosporanic acid, δ-(L-α-5-amino-5-carboxyvaleramido)-cephalosporanic acid (isocephalosporin C), adipoyl-7-ADCA, and adipoyl-7-ACA.

23. The method according to claim 21, wherein the carboxylic acid is selected from the group consisting of phenoxyacetic acid, phenylacetic acid, adipic acid, hexanoic acid, 2-thiopheneacetic acid and 3-thiopheneacetic acid.

24. The method according to claim 21, wherein the incubation takes place in the presence of $Mg^{2+}$ and ATP.

25. The method according to claim 21, wherein the incubation takes place in the presence of a reducing agent selected from the group consisting of dithiothreitol (DTT), mercaptoethanol, ascorbic acid and gluthathione.

26. The method according to claim 21, wherein the incubation takes place at a temperature between 10° C. and 60° C.

27. The method according to claim 21, wherein the incubation takes place at pH between 5.5 and 9.

28. The microbial host cell according to claim 13, wherein said host belongs to a genus selected from the group consisting of Bacillus, Streptomyces, Escherichia, Aspergillus, Cephalosporium, and Penicillin.

29. The microbial host cell according to claim 14, wherein said host belongs to a genus selected from the group consisting of Bacillus, Streptomyces, Escherichia, Aspergillus, Cephalosporium, and Penicillium.

30. The synthetase according to claim 1 which, in the synthesis of acyl-coenzyme A ester, has no substantial activity toward acetic acid.

31. The synthetase of claim 1 which has an isoelectric point higher than pH 7.25 and below up to about pH 12.

32. A method of purifying the synthetase according to claim 1 which comprises:

(a) obtaining a culture of a filamentous fungus selected from the group consisting of *Penicillin chrysogenum, Aspergillus nidulans*, and *Cephalosporium acremonium,*

(b) lysing the cells of said culture to obtain a cell extract, and (c) precipitating said synthetase from said cell extract.

33. The method according to claim 21, wherein the incubation takes place at a temperature of between about 15° C. and 50° C.

34. The method according to claim 21, wherein the incubation takes place at a temperature between 20° C. and 45° C.

35. The method according to claim 21, wherein the incubation takes place at about pH 8.

* * * * *